(12) United States Patent
Zheng

(10) Patent No.: US 10,945,693 B2
(45) Date of Patent: Mar. 16, 2021

(54) THREE-DIMENSIONAL IMAGING METHOD AND SYSTEM

(71) Applicant: Telefield Medical Imaging Limited, Hong Kong (HK)

(72) Inventor: Yongping Zheng, Hong Kong (HK)

(73) Assignee: Telefield Medical Imaging Limited, Hong Kong (HK)

(*) Notice: Subject to any disclaimer, the term of this patent is extended or adjusted under 35 U.S.C. 154(b) by 90 days.

(21) Appl. No.: 16/309,107

(22) PCT Filed: Jun. 9, 2017

(86) PCT No.: PCT/CN2017/087764
§ 371 (c)(1),
(2) Date: Dec. 11, 2018

(87) PCT Pub. No.: WO2017/215528
PCT Pub. Date: Dec. 21, 2017

(65) Prior Publication Data
US 2019/0307409 A1 Oct. 10, 2019

(30) Foreign Application Priority Data
Jun. 15, 2016 (CN) .......................... 201610427021.0

(51) Int. Cl.
*A61B 6/00* (2006.01)
*A61B 5/00* (2006.01)
(Continued)

(52) U.S. Cl.
CPC .......... *A61B 6/5205* (2013.01); *A61B 5/0033* (2013.01); *A61B 6/00* (2013.01);
(Continued)

(58) Field of Classification Search
None
See application file for complete search history.

(56) References Cited

U.S. PATENT DOCUMENTS

| 2002/0183610 | A1* | 12/2002 | Foley | ................... A61B 8/5238 600/407 |
| 2005/0078861 | A1* | 4/2005 | Usikov | ................. G06T 11/006 382/131 |
| 2012/0189178 | A1* | 7/2012 | Seong | ..................... G06T 19/00 382/128 |

FOREIGN PATENT DOCUMENTS

| CN | 101689298 A | 3/2010 |
| WO | WO-2008078259 A2 * | 7/2008 ............. A61B 5/417 |

OTHER PUBLICATIONS

International Search Report of PCT Patent Application No. PCT/CN2017/087764 dated Sep. 1, 2017.

\* cited by examiner

*Primary Examiner* — Suhail Khan

(57) ABSTRACT

Target-oriented three-dimensional imaging method and system are provided. The method comprises: determining, on a scanning object, a portion comprising a scanning target, forming an existing initial three-dimensional structure of the scanning target; scanning the portion comprising the scanning target to form a series of two-dimensional images with spatial location and orientation information; adjusting the initial three-dimensional structure of the scanning target or the local portion of the scanning target; when the initial three-dimensional structure is scanned over, then performing adjustments according to an image obtained and displaying on a display device. The method and system only require some initial three-dimensional information of an imaging target to be able to use two-dimensional imaging to continuously scan a location of a scanning target, adjust an original shape of the target to obtain an actual size, position, and detail of the target, and form a complete three-dimensional image of the target.

10 Claims, 5 Drawing Sheets

(51) Int. Cl.
*A61B 6/03* (2006.01)
*G16H 30/40* (2018.01)
*A61B 6/02* (2006.01)

(52) U.S. Cl.
CPC ............... *A61B 6/03* (2013.01); *A61B 6/466* (2013.01); *A61B 6/022* (2013.01); *A61B 6/505* (2013.01); *G16H 30/40* (2018.01)

THREE-DIMENSIONAL IMAGING METHOD AND SYSTEM

TECHNICAL FIELD

The present application relates to the field of three-dimensional imaging of the biological objects, and more particularly, relates to a target-oriented three-dimensional imaging method and system.

BACKGROUND

Three-dimensional imaging of biological objects is widely used in medicine, including CT, magnetic resonance imaging and the like. Recently, the use of ultrasound imaging to achieve three-dimensional imaging has also been used more and more. For example, three-dimensional imaging of the fetus and heart has come into the practical use. Ultrasound imaging of bone structures is also evolving. Compared to the heart and fetus, the human bone surface strongly reflects the ultrasound, making it difficult to image the structure below the bone surface, while the bones of the fetus are not calcified, so the ultrasound can penetrate. Therefore, ultrasound, optical tomography, photoacoustic imaging, and other similar methods of imaging an object with a skeletal structure all face this problem. For example, when scanning a human spine bone, a three-dimensional ultrasound scan from the back can only obtain images of the surface of the spinous process bone and the transverse bone but not images of the entire spine bone, because the vertebral body is on the other side, thereby greatly limiting the effect of three-dimensional imaging. On the other hand, we know the approximate shape of each section of spine. In addition, other methods such as CT and MRI can also obtain the basic three-dimensional structure of the spine.

SUMMARY

Aiming at the problems of ultrasonic three-dimensional imaging existing in the prior art, a three-dimensional imaging of a biological object is proposed, which can utilize the basic three-dimensional structure of the biological object on the one hand and utilize such as the ultrasound technology to perform two-dimensional scanning imaging on biological objects on the other hand. Thereby a three-dimensional imaging method and system for biological objects are proposed, which can reduce the scanning operation required for imaging and the use of radiation imaging methods on organisms thus reducing damage to living organisms.

A three-dimensional imaging method according to one aspect of the present application is provided, comprising following steps:

S1) determining, on a scanning object, a portion comprising a scanning target using a three-dimensional scanning;

S2) forming, on a basis of determined portion of the scanning object, an existing initial three-dimensional structure of the scanning target;

S3) scanning the portion comprising the scanning target to form a series of two-dimensional images with spatial location and orientation information;

S4) referring to image information related to the scanning target or a local portion of the scanning target within an image, adjusting the initial three-dimensional structure of the scanning target or the local portion of the scanning target;

S5) repeating steps S3) and S4) until the whole initial three-dimensional structure of the scanning target is scanned over, and performing adjustments according to an image obtained;

S6) displaying a final three-dimensional structure image of the scanning target after adjustments on a display device.

The three-dimensional imaging method of the present application further comprises a step of continuously displaying the initial three-dimensional structure of the scanning target and the adjusted three-dimensional structure during the two-dimensional scanning imaging process.

In the three-dimensional imaging method of the present application, the initial three-dimensional structure of the scanning target refers to a known representative three-dimensional anatomical structure of a certain portion of a human body.

In the three-dimensional imaging method of the present application, the initial three-dimensional structure of the scanning target refers to a representative three-dimensional anatomical structure corresponding to human bodies of different ages and genders.

In the three-dimensional imaging method of the present application, the initial three-dimensional structure of the scanning target is obtained by other means implemented on the scanning target, wherein the other means include performing a CT or MRI scan on the scanning target of human body and storing it in a database in advance.

In the three-dimensional imaging method of the present application, the adjustment of the initial three-dimensional structure of the scanning target or the local portion of the scanning target comprises a spatial location, an orientation, a size, and a relative proportion.

In the three-dimensional imaging method of the present application, the adjustment of the initial three-dimensional structure of the scanning target or the local portion of the scanning target is a deformable or non-deformable adjustment.

In the three-dimensional imaging method of the present application, the image information for controlling the adjustment in the step S4) comprises a characteristic point, a characteristic line, a characteristic face, a characteristic body of the scanning target or the local portion of the scanning target, or a combination thereof.

In the three-dimensional imaging method of the present application, the final three-dimensional structure image of the scanning target in the step S6) further comprises a characteristic label used by the adjustment.

A three-dimensional imaging system according to another aspect of the present application is provided, comprising:

an imaging device for acquiring two-dimensional images of a scanning target on a determined portion;

a space locating device for forming spatial location and orientation of each two-dimensional image from the imaging device;

a database for providing a initial three-dimensional structure of the scanning target;

a feature extraction unit for extracting characteristic information in the two-dimensional images or three-dimensional images formed by the two-dimensional images;

an adjustment unit for adjusting the initial three-dimensional structure of the scanning target using the characteristic information;

a display device for displaying the two-dimensional images and a three-dimensional structure of the scanning target.

By implementing the target-oriented three-dimensional imaging method and system provided by the present application, the three-dimensional imaging can be assisted by using known approximate three-dimensional structures of the scanning target and the adjustment of the two-dimensional images. The method of the present application can also be applied to other similar imaging methods, such as optical tomography, photoacoustic imaging, terahertz imaging, and the like. Since the three-dimensional imaging of the present application adopts target orientation, only some initial information of the imaging target should be needed. For example, when the imaging target is a certain bone of the human body, its approximate original shape can be known, but its specific size, position and detail cannot be got. Using the method of the present application, by means of continuously scanning the position of the target though the two-dimensional imaging, and adjusting the original shape of the target; the specific size, position and detail of the target are obtained, and an overall three-dimensional image of the target is formed. During the scanning process, the operator can continuously see the progress of the scanning through the display device, including the portions that have been scanned, the portions that have not been scanned and the quality of the images, so that useful feedback information can be obtained to guide further scanning

DETAILED DESCRIPTION OF THE PREFERRED EMBODIMENT

The features of the method and system of the present application are further described in conjunction with the accompanying drawings and embodiments, wherein the embodiments are merely illustrative and not limiting.

The First Embodiment

Figure 1:
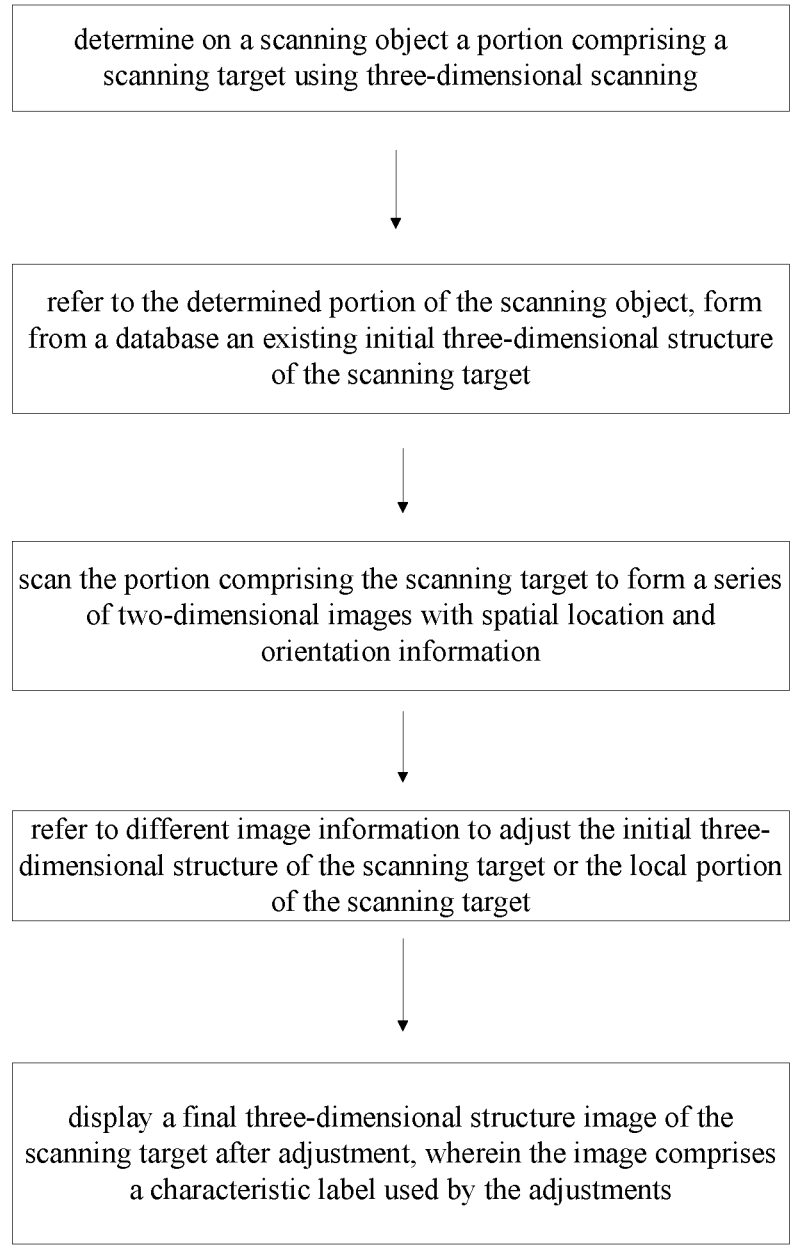
FIG. 1 is a schematic flow chart of a three-dimensional imaging method of a first embodiment of the present application.

In the first embodiment of the method of the present application, as shown in FIG. 1, the target-oriented three-dimensional imaging method provided by the present application includes the following steps.

Figure 2:
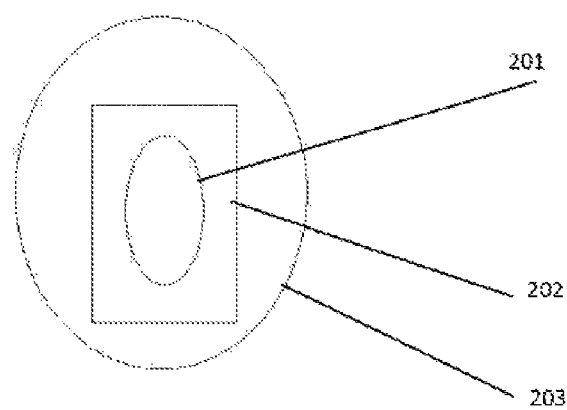
FIG. 2 is a schematic diagram showing a relationship between a scanning target and a scanning range in an embodiment of the method of the present application.

Step 101) determining, on a scanning object, a portion comprising a scanning target using three-dimensional scanning When performing the three-dimensional imaging of a specific patient scanning target, a scanning range 202 may be given according to the estimated scanning target position 201. As shown in FIG. 2, 201 is the estimated scanning target position, 202 is the given scanning range, and 203 is an area including the scanning target. In other words, for objects requiring three-dimensional imaging, the position to be scanned can be first estimated based on experience. For this, a scanning range 202 can be given on the human body or other living organisms, which can cover the position 201 of the estimated scanning target, and the area 203 is an area including the scanning target, as shown in FIG. 2.

Figure 3:
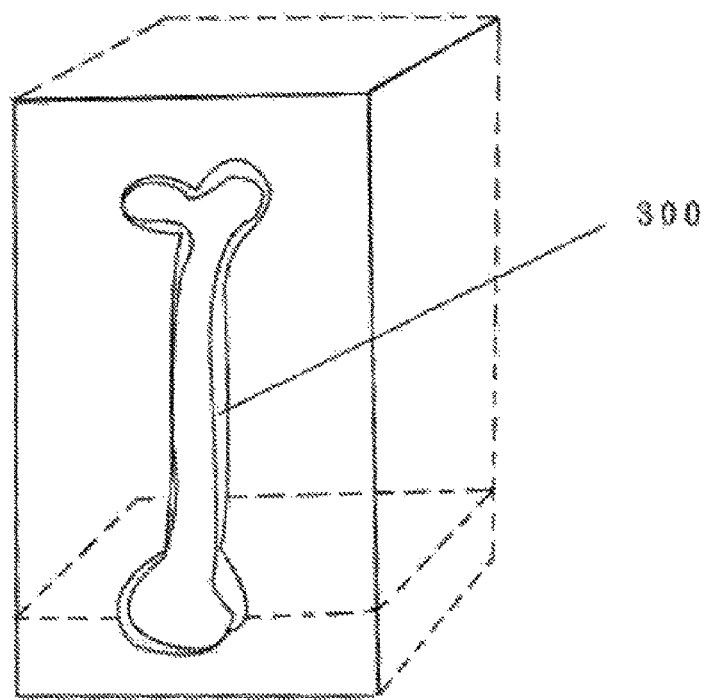
FIG. 3 is a three-dimensional structure image illustrating placement of a scanning target at a position of the scanning target in an embodiment of the method of the present application.

Step 102) on the basis of the determined portion of the scanning object, forming an existing initial three-dimensional structure of the scanning target from a database On the basis of the scanning range given in the step 101, a three-dimensional structure is extracted from the database pre-storing the three-dimensional structure of the scanning target as the initial three-dimensional structure 300 of the scanning target. As shown in FIG. 3, in the given scanning range 202, the initial three-dimensional structure image 300 of the scanning target is put. Wherein, the initial three-dimensional structure of the scanning target corresponding to the three-dimensional structure image 300 can be a known representative three-dimensional anatomical structure of a certain portion of human body which is pre-acquired and stored in a database. It also can be representative three-dimensional anatomical structures corresponding to human bodies of different ages and genders which are pre-acquired and stored in a database, or further can a be three-dimensional anatomical structure pre-obtained by other means and stored in a database. The other means include performing a CT or MRI scan on the scanning target of human body. Among them, the three-dimensional structure of different sources should have a data structure with uniform standards.

Figure 4:
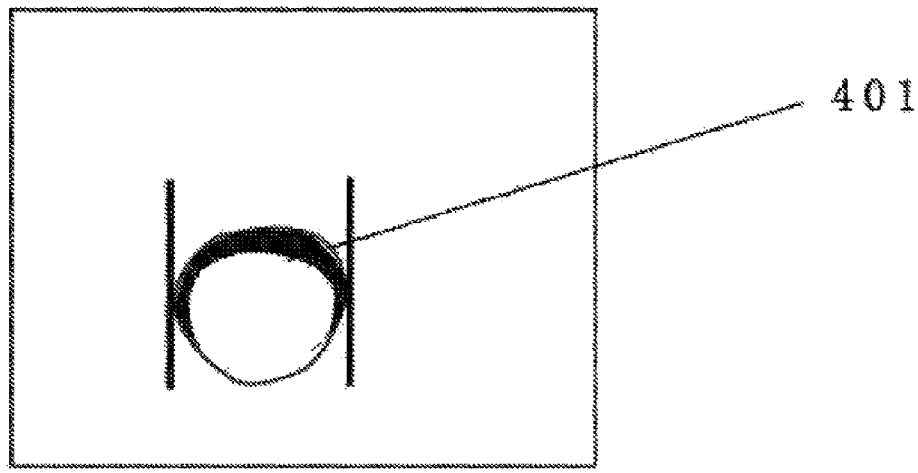
FIG. 4 is a cross-sectional view (a) of a three-dimensional structure image and an image (b) obtained by a two-dimensional ultrasonic method at the same position in the present embodiment.
Figure 4:
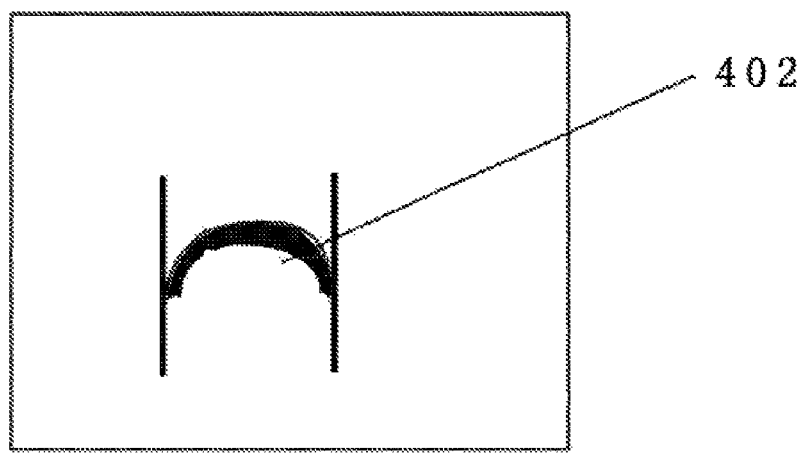

FIG. 4 (*a*) is a cross-sectional view showing the three-dimensional structure image of the initial form of the scanning target read from the database in the present embodiment.

Step 103) through ultrasound imaging technology, scanning the portion comprising the scanning target to form a series of two-dimensional images with different spatial location and/or orientation information Since the two-dimensional imaging can be performed within a given scan range from various angles, the most characteristic information about the scanning target can be obtained, as although some characteristic information may not be clearly imaged from one direction, however it may be clearer when imaging from another direction. Step 103 indicates that the two-dimensional imaging obtains as much information as possible by giving different directions and positions.

FIG. 4 (*b*) is an image obtained by two-dimensional ultrasound imaging at the same position of FIG. 4 (*a*). As the high-frequency ultrasound cannot penetrate the bone, the lower portion of the bone structure cannot be imaged. When comparing the two images, the structure of the scanning target can be globally or locally adjusted according to the curve ratios obtained from the corresponding positions.

Step 104) referring to image information related to the scanning target or a local portion of the scanning target within an image, adjusting the initial three-dimensional structure of the scanning target or the local portion of the scanning target In step 104), the image information for controlling the adjustment comprises a characteristic point, a characteristic line, a characteristic face, a characteristic body of the scanning target or the local portion of the scanning target, or a combination thereof.

Figure 5:
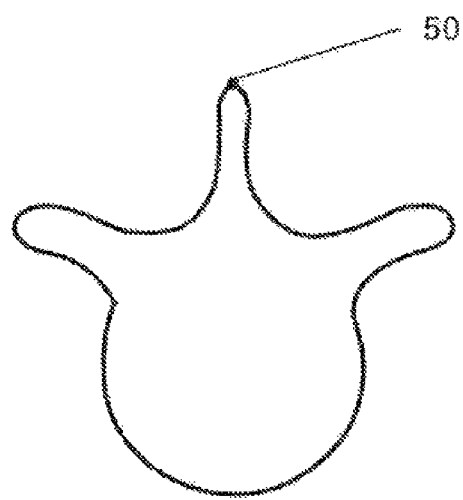
FIG. 5 is a schematic view showing a point on a scanning target in an embodiment of the method of the present application.

The point on the scanning target as shown in FIG. 5 may be some characteristic points on the scanning target, such as characteristic points formed on the image by human bones. FIG. 5 shows the spinous process apex 50 of the spine bone (scanning target) as a characteristic point of the spine bone.

Figure 6:
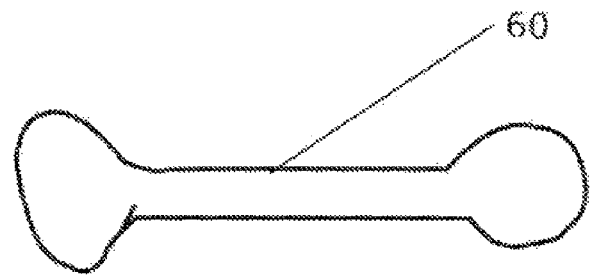
FIG. 6 is a schematic view showing a line on a scanning target in an embodiment of the method of the present application.

The line on the scanning target as shown in FIG. 6 may be some characteristic lines on the scanning target, for example, a straight line 60 formed on the image by the human bone. As shown in FIG. 6, the characteristic line may be a straight line or a curved line.

Figure 7:
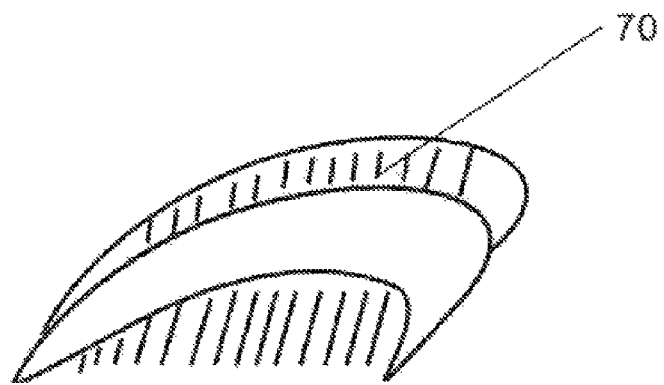
FIG. 7 is a schematic view showing a face on a scanning target in an embodiment of the method of the present application.

The surface on the scanning target shown in FIG. 7 may be some characteristic surfaces 70 on the scanning target. The characteristic surface may be a plane or a curved surface. The characteristic surface 70 shown in FIG. 7 is a curved characteristic surface.

Figure 8:
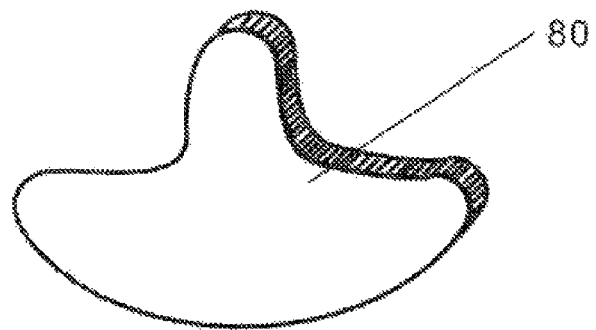
FIG. 8 is a schematic view showing the body on a scanning target in the embodiment of the method of the present application.

The body on the scanning target as shown in FIG. 8 may have some characteristic body 80.

Based on the characteristic points, lines, faces, and bodies of the scanning target, the adjustments including global or local translation, rotation, scaling, and or a combination thereof can be performed on the scanning target, for example, simultaneously panning and zooming.

Step 105) repeating steps S3) and S4) until the initial three-dimensional structure of the scanning target has been adjusted based on the obtained images The adjustment of the image here can be done off-line and completed after all the images are collected, reducing the time spent on the scanning target during scanning Step 106) displaying a final three-dimensional structure image of the scanning target after adjustment on a display device The final three-dimensional structure image of the scanning target further comprises a characteristic label used by the adjustment.

The Second Embodiment

The second embodiment comprises following steps:

Step 201) based on the scanning target, determining the scanning portion of the scanning object;

Step 202) forming a initial three-dimensional structure of a scanning target from a database;

Step 203) on the display device, displaying the initial three-dimensional structure and the structure information to be adjusted comprising a characteristic point, a characteristic line, a characteristic face, a characteristic body;

Step 204) changing the spatial location of the scanning probe by translation or (and) changing the orientation of the scanning probe by rotation, scanning the determined scanning portions and acquiring a series of two-dimensional images with different spatial location and orientation information of the scanning target; displaying the two-dimensional images obtained by scanning on the display device;

Step 205) referring to image information related to the scanning target or a local portion of the scanning target within an image, adjusting the initial three-dimensional structure; wherein the adjustment comprises one or more of spatial location, angle, size, and relative proportion;

Step 206) determining whether the two-dimensional images obtained in the step 204) have covered the initial three-dimensional structure of the scanning target and the three-dimensional structure of the known target has been adjusted, if so the process goes to Step 207, or else repeating the step 204 and the step 206;

Step 207) displaying a final three-dimensional structure image of the scanning target after adjustment on a display device.

The adjustment on the image in the steps 205-207) can be done off-line once after all the images are collected, which can reduce the scanning time.

In another embodiment, which is different from the second embodiment described above in that the adjustment in step 205 is a deformable adjustment, that is, the scanning of the target starts from the initial three-dimensional result, and each portion can be individually adjusted according to the information obtained in the image scanning, so that the various portions of the adjusted scanning target are not simply scaled. Deformable scaling is particularly useful for spinal bone distortion.

In another embodiment, which is different from the second embodiment described above in that after the three-dimensional structure is adjusted in step 205, a step may be added in which the three-dimensional structure of the adjusted scanning target is displayed in the display device each time. The operator can continuously see the progress of the scan, including the portion that has been scanned and the portion that has not been scanned, and the quality of the image, so that useful feedback information can be obtained to guide the further scanning In another embodiment, which is different from the second embodiment described above in that the final three-dimensional structure image of the scanning target in the step S6) further comprises a characteristic label used by the adjustment to facilitate the adjustment operation.

Figure 9:
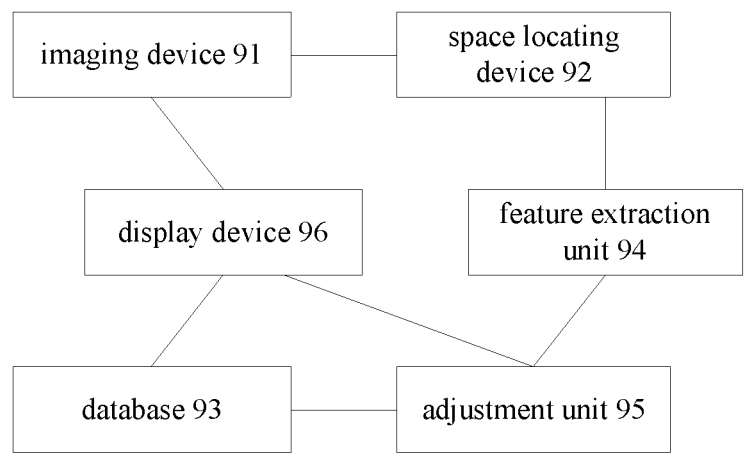
FIG. 9 is a schematic diagram illustrating a three-dimensional imaging system in accordance with an embodiment the present application.

In the embodiment of a three-dimensional imaging system of the present application illustrated in FIG. 9, the following components are comprised: 1) an imaging device 91 for acquiring two-dimensional images of a scanning target on a determined portion, in this embodiment, this imaging device can be an ultrasound scan imaging device; 2) a space locating device 92 for acquiring spatial location and angle of each two-dimensional image from the imaging device; when the imaging device performs continuous scanning imaging on the determined portion, the space locating device 92 records the corresponding two-dimensional images formed by the scanning imaging as a basis for adjusting the initial three-dimensional structure; 3) a database 93 for providing an initial three-dimensional structure of the scanning target; here, all kinds of the initial three-dimensional structure database of the scanning target are pre-stored in the database; 4) a feature extraction unit 94 for extracting characteristic information in the two-dimensional images or three-dimensional images formed by the two-dimensional images; the characteristic information here can be a point, a line, a face or a body; 5) an adjustment unit 95 for adjusting the initial three-dimensional structure of the scanning target using the characteristic information; the adjustment here comprises one or more of the spatial location, orientation, size, and relative proportion; 6) a display device 96 for displaying the two-dimensional images and a three-dimensional structure of the scanning target. When obtaining the initial three-dimensional structure from the database, the display device 96 displays the three-dimensional structure image; while when obtaining the two-dimensional images from the imaging device 91, the display device 96 displays the two-dimensional images. When obtaining the three-dimensional structure adjusted by the adjustment unit 95, the display device 96 displays the three-dimensional structure image adjusted with the characteristic information.

The target-oriented three-dimensional imaging method and system of the present application utilizes an existing initial three-dimensional structure and readily available two-dimensional images having different spatial locations and orientations to adjust the initial three-dimensional structure to obtain three-dimensional imaging of the scanning target. The implementation process of this kind of three-dimensional imaging has no harm to the human body, and the adjustment of the three-dimensional structure can be processed in the background by quickly completing the imaging of the two-dimensional image, which reduces the time for detecting the scanning, and can present richer details of the three-dimensional images.

The above is only a preferred embodiment of the method and system of the present application. It should be understood that those skilled in the art can make modifications or changes in accordance with the above description, and all such improvements and modifications should fall within the scope of the appended claims.

The invention claimed is:

1. A three-dimensional imaging method comprising following steps:
    S1) determining, on a scanning object, a portion comprising a scanning target using a three-dimensional scanning;
    S2) forming, on a basis of determined portion of the scanning object, an existing initial three-dimensional structure of the scanning target;
    S3) scanning the portion comprising the scanning target within a given scan range from various angles to form a series of two-dimensional cross-sectional images with different spatial location and orientation information;
    S4) referring to image information related to the scanning target or a local portion of the scanning target within the two-dimensional cross-sectional images, adjusting the initial three-dimensional structure of the scanning target or the local portion of the scanning target;
    S5) repeating steps S3) and S4) until the whole initial three-dimensional structure of the scanning target is scanned over, and performing adjustments according to an image obtained;
    S6) displaying a final three-dimensional structure image of the scanning target after adjustments on a display device.

2. The three-dimensional imaging method according to claim 1, wherein, further comprises a step of continuously displaying the initial three-dimensional structure of the scanning target and the adjusted three-dimensional structure during the two-dimensional scanning imaging process.

3. The three-dimensional imaging method according to claim 1, wherein, the initial three-dimensional structure of the scanning target refers to a known representative three-dimensional anatomical structure of a certain portion of a human body, and the representative three-dimensional anatomical structure is pre-stored in a database.

4. The three-dimensional imaging method according to claim 1, wherein, the initial three-dimensional structure of the scanning target refers to a representative three-dimensional anatomical structure corresponding to human bodies of different ages and genders, and the representative three-dimensional anatomical structure of different ages and genders is pre-stored in a database.

5. The three-dimensional imaging method according to claim 1, wherein, the initial three-dimensional structure of the scanning target is obtained by other means implemented on the scanning target, and the other means include performing a CT or MRI scan on the scanning target of human body and storing it in a database in advance.

6. The three-dimensional imaging method according to claim 1, wherein, the adjustment of the initial three-dimensional structure of the scanning target or the local portion of the scanning target comprises a spatial location, an orientation, a size, and a relative proportion.

7. The three-dimensional imaging method according to claim 1, wherein, the adjustment of the initial three-dimensional structure of the scanning target or the local portion of the scanning target is a deformable or non-deformable adjustment.

8. The three-dimensional imaging method according to claim 1, wherein, the image information for controlling the adjustment in the step S4) comprises a characteristic point, a characteristic line, a characteristic face, a characteristic body of the scanning target or the local portion of the scanning target, or a combination thereof.

9. The three-dimensional imaging method according to claim 1, wherein, the final three-dimensional structure image of the scanning target in the step S6) further comprises a characteristic label used by the adjustment.

10. A three-dimensional imaging system comprising:
    an imaging device for acquiring two-dimensional cross-sectional images of a scanning target on a determined portion by scanning the determined portion within a given scan range from various angles;
    a space locating device for acquiring spatial location and orientation of each two-dimensional cross-sectional image from the imaging device;
    a database for providing an initial three-dimensional structure of the scanning target;
    a feature extraction unit for extracting characteristic information in the two-dimensional cross-sectional images or three-dimensional images formed by the two-dimensional cross-sectional images;
    an adjustment unit for adjusting the initial three-dimensional structure of the scanning target using the characteristic information;
    a display device for displaying the two-dimensional cross-sectional images and a three-dimensional structure of the scanning target.

* * * * *